United States Patent [19]
Persky

[11] Patent Number: 5,163,897
[45] Date of Patent: Nov. 17, 1992

[54] INCONTINENT PROTHESIS AND METHOD

[76] Inventor: Lester Persky, 15 Bluehill Ave., Naples, Fla. 33463

[21] Appl. No.: 427,002

[22] Filed: Oct. 25, 1989

[51] Int. Cl.$^5$ ............................................... A61F 2/02
[52] U.S. Cl. ............................ 600/31; 128/DIG. 25; 623/12
[58] Field of Search ........................... 600/30, 31, 29; 128/DIG. 25; 623/12

[56]  References Cited

U.S. PATENT DOCUMENTS

| | | | |
|---|---|---|---|
| 4,187,851 | 2/1980 | Hoauser . | |
| 4,386,601 | 6/1983 | Trick . | |
| 4,412,530 | 11/1983 | Burton . | |
| 4,417,567 | 11/1983 | Trick . | |
| 4,419,985 | 12/1983 | Trick . | |
| 4,428,365 | 1/1984 | Hakky | 600/31 |
| 4,549,530 | 10/1985 | Finney | 600/31 |
| 4,549,531 | 10/1985 | Trick . | |
| 4,573,985 | 3/1986 | Finney . | |
| 4,640,688 | 2/1987 | Hoauser . | |

Primary Examiner—David J. Isabella
Assistant Examiner—G. Gualtieri
Attorney, Agent, or Firm—Watts, Hoffman, Fisher & Heinke

[57] ABSTRACT

A urinary incontinence prosthesis in the form of an inflatable implant. The implant includes a uniquely configured balloon having a central portion for positioning adjacent the patient's urethra and pairs of claw like arms partially circumscribing the patient's corpus cavernosa. The process for use comprises implanting the balloon and suturing apertured tabs to a patient's tunica to maintain the prosthesis device in its desired position. A pump/reservoir is positioned in the patient's scrotum and connected in fluid communication with the prosthesis by a suitable tube. The entire device is made of biocompatible implantable material.

14 Claims, 4 Drawing Sheets

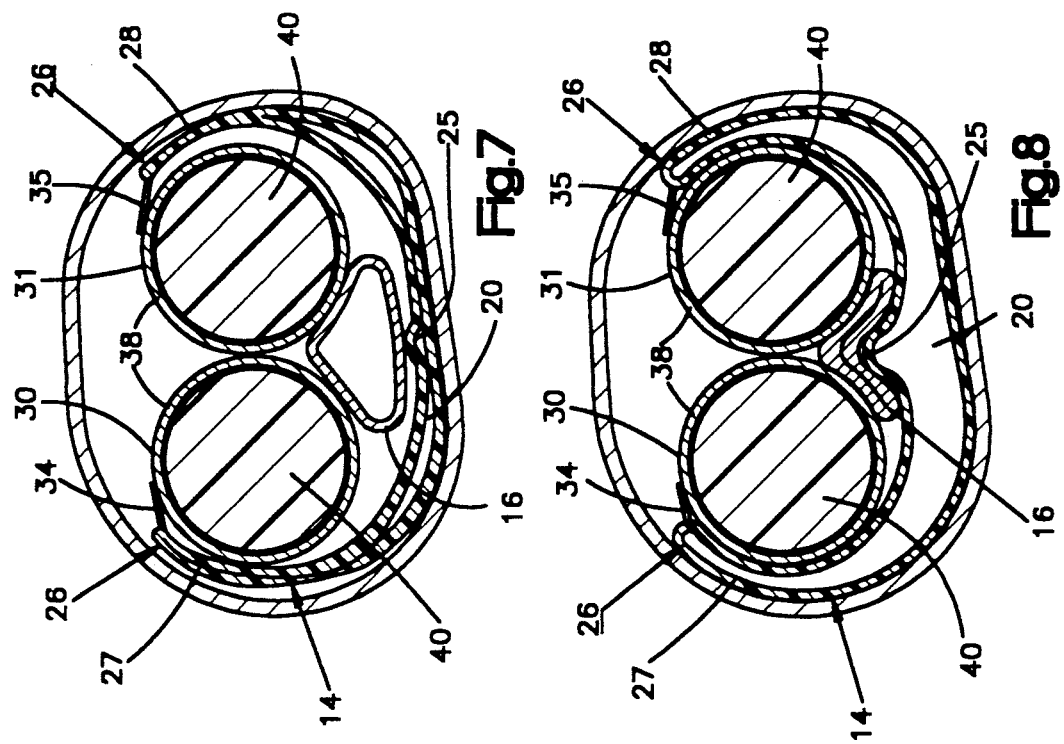
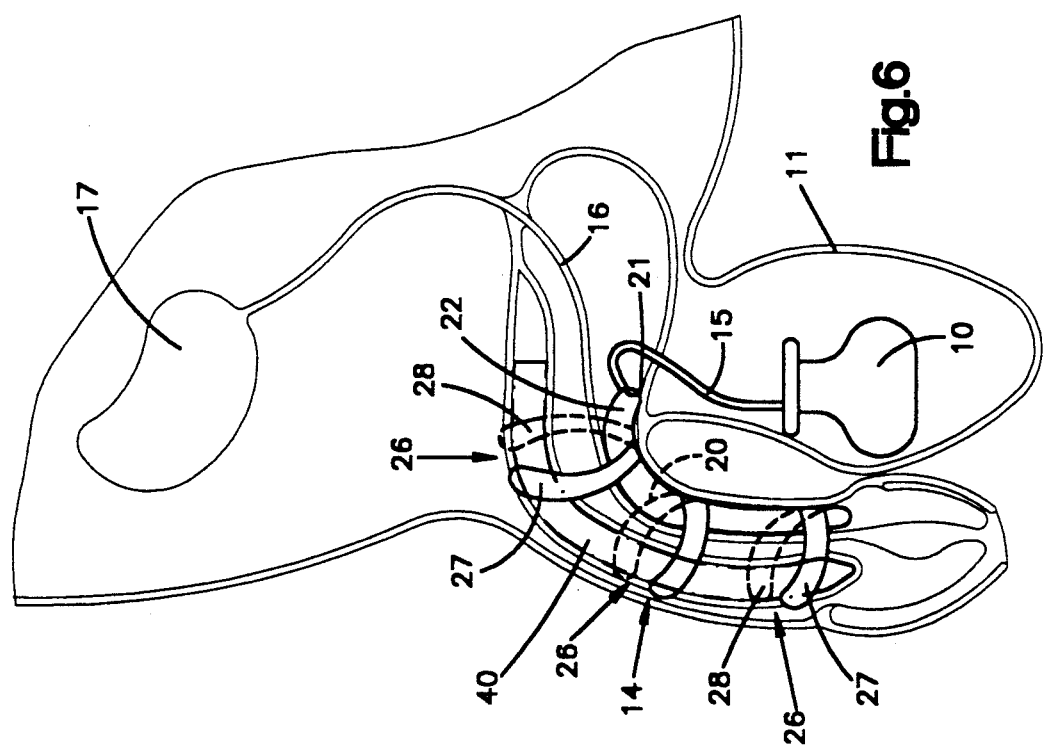

INCONTINENT PROTHESIS AND METHOD

TECHNICAL FIELD

This invention relates to an incontinent prosthesis and a novel method of controlling male incontinence.

BACKGROUND ART

To persons suffering from it, urinary incontinence is both an embarrassment and a hygienic problem. The problem results from malfunctioning urethral sphincters. The malfunctioning can result from a congenital malformation or trauma to or disease of sphincter nerves or muscles. When the urethral sphincter fails to function properly uncontrolled or inadequately controlled bladder drainage can occur.

There have been many attempts to provide an artificial sphincter for patients suffering from a malfunctioning sphincter. These include proposals for implantable and inflatable urinary incontinence prostheses none of which have been fully satisfactory.

There have also been attempts at other methods of control including elastic constrictors, magnetically controlled urethra compressors, and clamps such as the so-called Cunningham clamp and improvements on it. All these attempts utilize devices which can themselves cause trauma, irritation and generalized injury to other tissues.

Other approaches have utilized catheters which are coupled to the patient to provide, for example, a drain tube into a vessel attached to the patient's leg. Such attempts have been undesirable for hygienic and other reasons.

Most prior attempts restricted the urethra until a patient took some action to physically relieve the restriction. The action might be the release of a clamp, the movement of a magnet, the stretching of an elastic, or the decompression of an inflatable device. Other proposals relied on the muscles of the patient's bladder to provide a force which would overcome the restriction and allow the passage of urine.

DISCLOSURE OF THE INVENTION

The present invention is directed to an improved implantable urinary incontinent prosthesis. In a prosthesis made in accordance with this invention, a uniquely configured balloon of imperforate biocompatible material is provided. The balloon includes a urethra compressing portion which is adapted for implantation against the patient's urethra. This portion is an elongated, inflatable, proximal portion with a fluid supply opening at one end and an enlargement adjacent the opening for enhancing the delivery of fluid.

Spaced pairs of curved anchoring portions are coupled to the compressing portion. The anchoring portions of each pair extend in diametric opposition from and in fluid communication with the compressing portion. The anchoring portions of each pair are each adapted to partially circumscribe an associated corpus cavernosum. The anchoring portions, when inflated, supply a force additive to that of the compressing portion to compress, as contrasted with restrict, the urethra of a patient to stop of the flow of urine therethrough.

At least certain of the portions include apertured projections which extend from the portions for suturing to a patient's tunica to anchor the prosthesis in place.

A pump/reservoir of biocompatible material is positioned in the patient's scrotum. A connecting tube interconnects the supply opening of the proximal portion of a balloon to the pump/reservoir for transmitting fluid to and from the balloon as the pump/reservoir is manipulated to inflate and deflate the balloon cyclically.

In certain patients the corpus cavernosa may be incapable of cooperating with the anchoring portions to produce sufficient forces additive to those generated by the compressing portion. Under such circumstances elongated support members of a biocompatible material of sufficient rigidity for the intended use may be implanted. The support member implants are positioned within the corpora cavernosa of a patient.

Accordingly, the object of the invention is to provide a novel and improved incontinence prosthesis and a method of controlling urinary incontinence in a male patient.

BRIEF DESCRIPTION OF THE DRAWINGS

FIG. 6 is a view corresponding to FIG. 1 with support members having been implanted; and FIGS. 7 and 8 are cross sectional views showing the support members implanted and the prosthesis device in deflated and inflated conditions respectively.

BEST MODE FOR CARRYING OUT THE INVENTION

Figure 1:
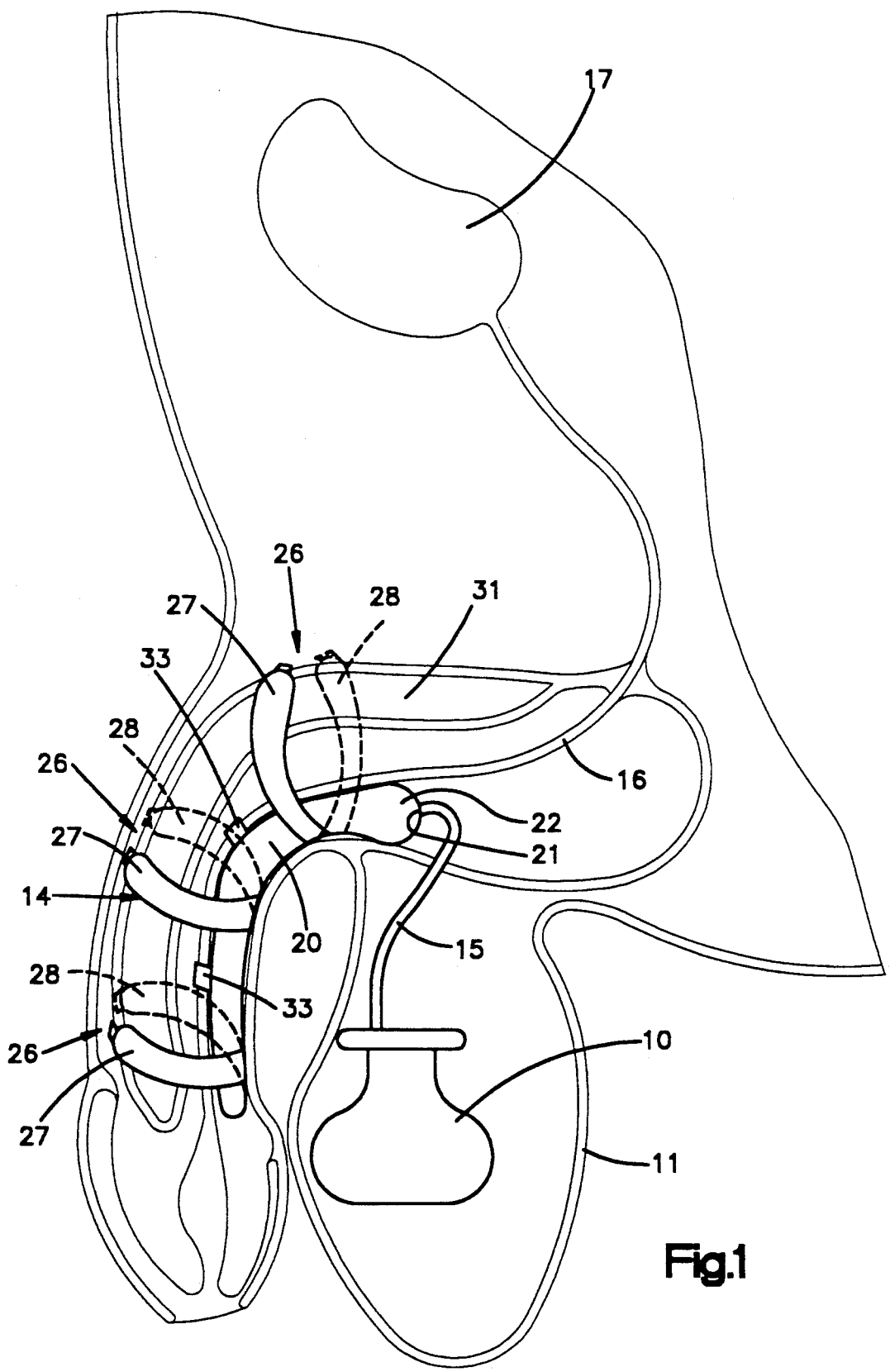
FIG. 1 is a perspective view of the prosthesis device of this invention implanted in a patient and in a deflated condition.
Figure 2:
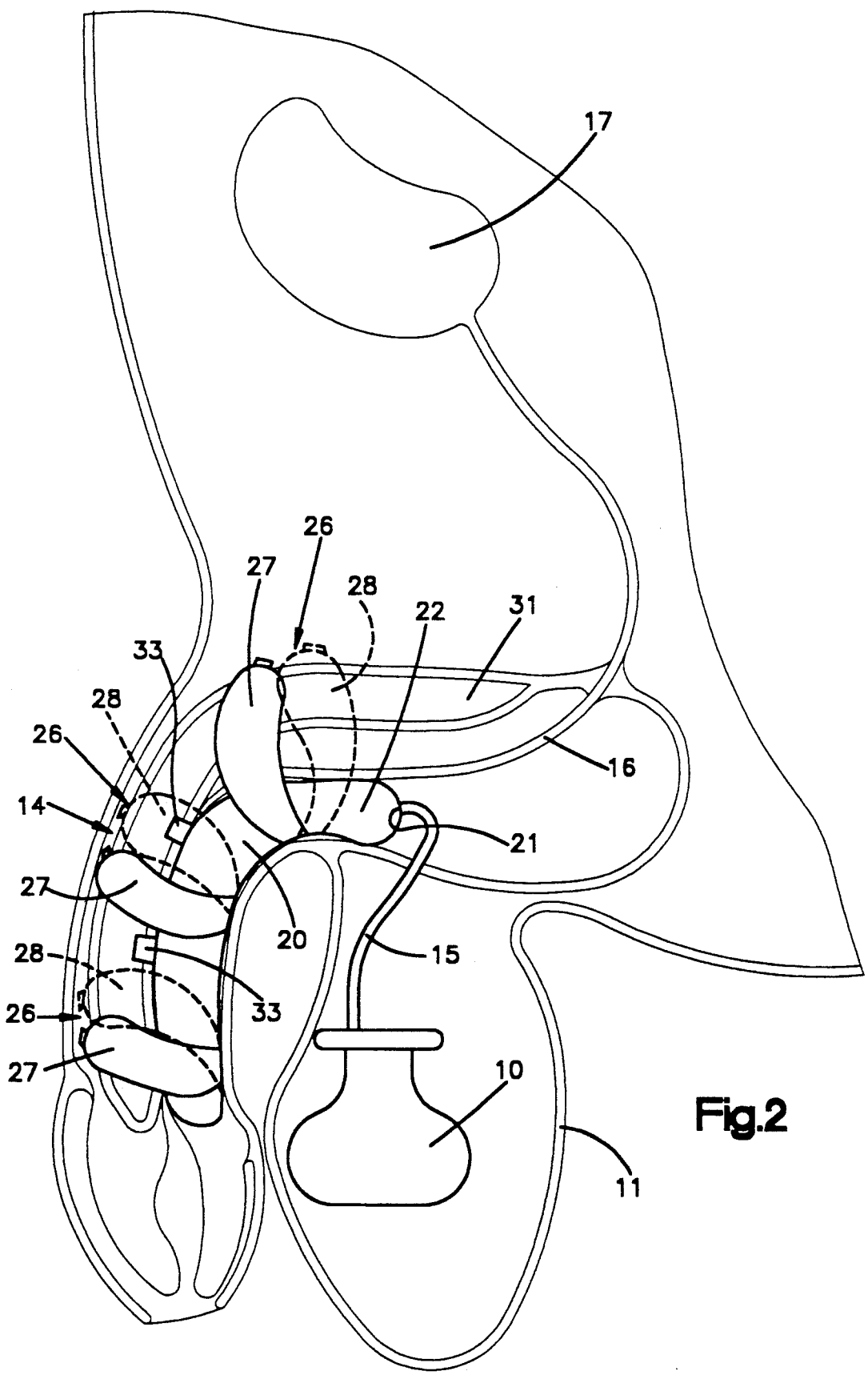
FIG. 2 is a view corresponding to FIG. 1 showing the prosthesis device in the inflated condition.

Referring to the drawings and to FIGS. 1 and 2 in particular, a pump/reservoir 10 is provided. The pump/reservoir is made of a biocompatible material and positioned within a patient's scrotum 11. A suitable pump/reservoir is currently sold commercially by Mentor Corporation of Golita, Calif. as a pump/reservoir component of a prosthesis for an impotent patient. The penile prosthesis sold by Mentor Corporation as model GFS Mark II is one such prosthesis.

An implantable prosthesis is shown generally at 14. The prosthesis 14 is a uniquely configured balloon made of an imperforate biocompatible material to provide fluid containing walls. A suitable material is a mesh reinforced silicone elastomer. A tube 15 interconnects the pump/reservoir 10 and the prosthesis 14. The tube 15 is preferably made of the same imperforate, biocompatible material as the prosthesis.

A patient's urethra is illustrated at 16. The urethra is connected to a bladder 17.

The prosthesis 14 includes a central compressing portion 20 which is an elongated, inflatable, proximal portion. This proximal portion when in use is positioned adjacent the urethra 16. The central portion 20 includes a fluid opening 21 in fluid conducting communication with the tube 15. The central portion 20 also includes an enlarged portion 22 provided adjacent the opening 21 for facilitating the transfer of fluid into and out of the prosthesis 14.

Figure 5:
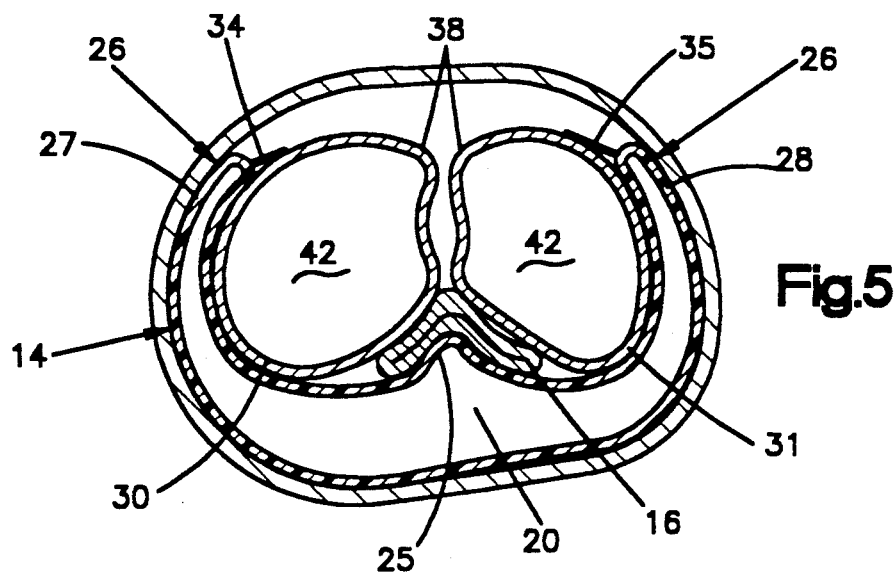

The central portion 20 includes a raised central compressor part 25 best seen in FIGS. 5 and 8. The compressor part 25 extends longitudinally of the urethra and is positioned centrally, transversely speaking, of the urethra to provide effective compression of the urethra and concomitant stoppage of urine flow when the implanted device is inflated.

Three pairs of anchoring portions 26 are provided. The pairs of anchoring portions are connected to the central portion at locations spaced longitudinally of the central portion. The anchoring portions of each pair are curved arms 27, 28. Each of the arms is curved to partially circumscribe the patient's corpus cavernosa 30, 31 respectively as is best seen in FIGS. 4, 5, 7, and 8. The arms 27, 28 of each pair are connected to the central portion 20 extending in diametric opposition, transversely from the central portion. Cavities defined by the arms are in fluid communication with the central portion to define a fluid chamber.

When inflated the arms 27, 28 assume a claw like configuration as is best illustrated in FIGS. 2, 5, and 8. When inflated the arms coact against the corpus cavernosa and transmit a force to the central portion which is additive to the compressive force supplied to the urethra by the central portion.

The central portion 20 is equipped with apertured tabs 33. Corresponding apertured tabs 34, 35 are connected to the arms 27, 28 respectively. The apertured tabs are sutured to a patient's tunica 38 to anchor the prosthesis device in its implanted position.

Figure 3:
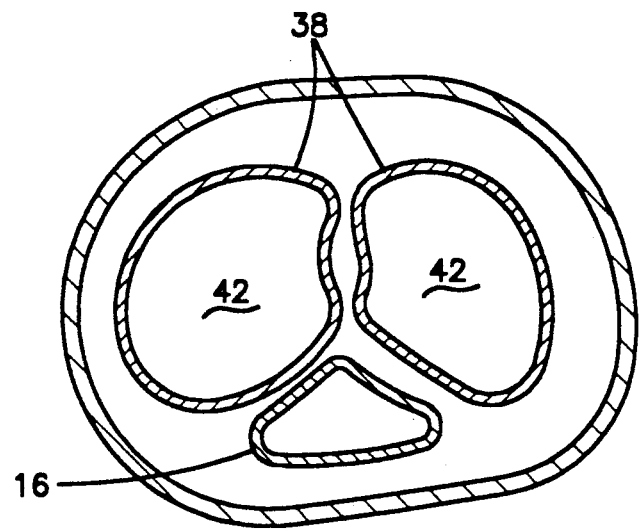
FIGS. 3-5 are cross sectional views of a male organ in the case of FIG. 3 prior to implant, in FIG. 4 with the prosthesis device deflated, and in FIG. 5 with the prosthesis device inflated.
Figure 4:
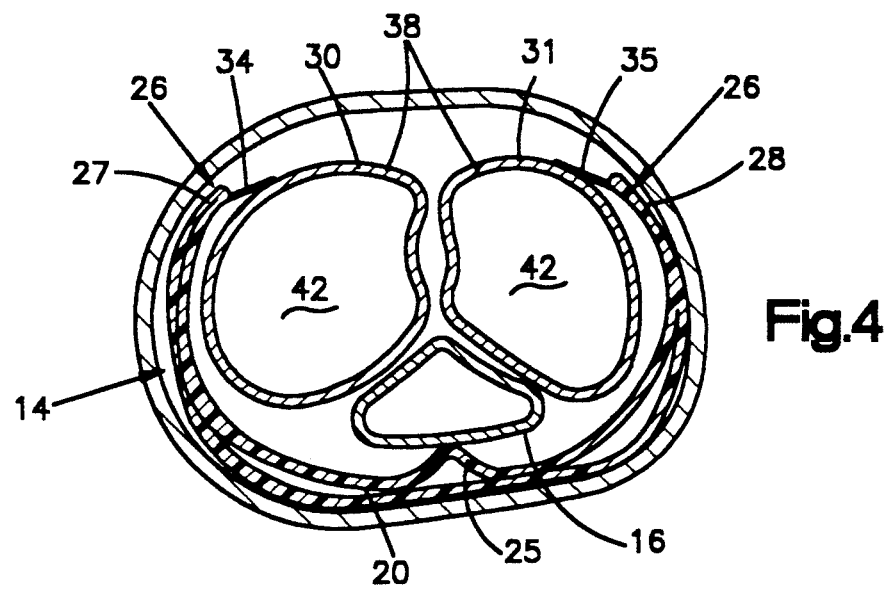

Referring to FIGS. 6 and 7 a pair of biocompatible support members 40 are provided. The support members 40 are implanted in a patient's corpora cavernosa 42 (FIGS. 3-5). The support members 40 are used in that situation where the condition of the patient is such that the coaction of the inflatable arm and corpus cavernosa will not be adequate to produce sufficient force additive to the force of the central portion to the effect a closing of urethra.

In the treatment of a patient afflicted with urinary incontinence, the prosthesis device 14 is surgically implanted in the patient's penis. The central proximal portion is positioned adjacent the urethra with its raised central part 25 centrally located transversely speaking. The tabs 33 are then sutured to the patient's tunica.

The arms 27, 28 are then positioned in their partial circumscribing relationship with the corresponding corpus cavernosum 30, 31. The anchoring arm tabs 34, 35 are then sutured to the tunica.

The pump/reservoir 10 is positioned in the patient's scrotum 11. While it may be sutured in place, typically physicians do not do so when positioning a pump/reservoir in a scrotum.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

I claim:

1. A urinary incontinence prosthesis for a male patient comprising:
   (a) a pump of biocompatible material; and
   (b) an inflatable balloon of biocompatible material, means connecting the balloon in fluid communication with the pump, the pump including a reservoir for inflating and deflating the balloon, the balloon comprising:
      (i) a relatively elongate urethra compressing portion adapted for implantation adjacent a urethra and when inflated to close such urethra to the passage of urine and to deflate upon actuation of the pump to permit the passage of urine; and
      (ii) a pair of curved anchoring portions projecting transversely and oppositely from the compressing portion, the curved portions being respectively adapted to partially circumscribe a corresponding corpus cavernosum, the curved portions being in fluid communication with the compression portion and adapted to inflate concurrently and thereby respectively coact against the corresponding corpus cavernosum and supply a force additive to that of the compression portion to close such urethra.

2. The prosthesis of claim 1 wherein there are a plurality of pairs of anchoring portions.

3. The prosthesis of claim 2 wherein the pairs are spaced from one another.

4. The prosthesis of claim 1 wherein the anchoring portions project in a diametric opposition from the compressing portion.

5. The prosthesis of claim 1 wherein the balloon includes projections for suturing to the tunica of a patient's corpus cavernosum.

6. The prosthesis of claim 1 further including a pair of biocompatible support members adapted for implantation in a patient's corpora cavernosa to coact with the anchoring portions in providing such additive force.

7. An inflatable implant for controlling urinary incontinence in a male patient:
   (a) an elongated, inflatable proximal portion having a fluid supply opening near one end, the opening being adapted for connection to a pump mechanism;
   (b) a plurality of pairs of inflatable, curved, anchoring portions connected to the proximal portion, the anchoring portions of each pair projecting laterally and oppositely from the proximal portion;
   (c) the pairs of anchoring portions being longitudinally spaced from one another along the proximal portion;
   (d) the portions collectively defining an internal fluid chamber and collectively having, apart from the supply opening, imperforate fluid containing walls and, the portions being formed of a biocompatible implantable material.

8. The implant of claim 7 wherein the anchoring portions are of a configuration curved in transverse cross section and adapted when inflated and in use to engage the corpus cavernosa of a patient in compressive relationship whereby to establish a force additive to that of the concurrently inflated proximal portion to compress and close off the patient's urethra.

9. The implant of claim 7 wherein the implant includes projections for suturing to the tunica of a patient's corpus cavernosum.

10. The implant of claim 7 wherein each anchoring portion has an apertured projection adapted to be sutured to the tunica of a patient's corpus cavernosa without rupture of the imperforate walls.

11. The prosthesis of claim 7 wherein the proximal portion includes an enlarged part adjacent the supply opening.

12. A method of implanting urinary incontinence in a male patient which comprises implanting an inflatable balloon in the penis of a patient including the steps of:
   (a) positioning an elongate, inflatable proximal portion adjacent the urethra;

(b) positioning a pair of laterally and oppositely directed inflatable arm portions of the balloon respectively in partially circumscribing relationship with an associated corpora cavernosum; and (c) suturing tabs projecting from certain of the inflatable portions to the tunica of the patient's corpora cavernosum to secure the balloon in its implanted position.

13. The method of claim 12 including the further step of implanting a pump in the patient's scrotum and providing a fluid connection between the pump and the balloon for transferring fluid from one to the other and return.

14. The method of claim 12 including the further step of respectively implanting a pair of biocompatible support members in the patient's corpora cavernosa.

* * * * *